United States Patent

Boland

[11] Patent Number: 5,499,420
[45] Date of Patent: Mar. 19, 1996

[54] BRUSH HOLDER FOR A TOOTHBRUSH

[75] Inventor: Bernhard Boland, Frankfurt, Germany

[73] Assignee: Braun Aktiengesellschaft, Kronberg, Germany

[21] Appl. No.: 362,542

[22] PCT Filed: Jun. 30, 1993

[86] PCT No.: PCT/EP93/01685

§ 371 Date: Jan. 4, 1995

§ 102(e) Date: Jan. 4, 1995

[87] PCT Pub. No.: WO94/02047

PCT Pub. Date: Feb. 3, 1994

[30]     Foreign Application Priority Data

Jul. 15, 1992 [DE] Germany ............ 42 23 196.5

[51] Int. Cl.⁶ .................. A61C 17/26; A46B 13/02
[52] U.S. Cl. ............... 15/22.1; 15/167.1; 15/176.6
[58] Field of Search ................ 15/167.1, 172, 15/173, 176.1, 176.4, 176.5, 176.6, 178, 23, 28

[56]           References Cited

U.S. PATENT DOCUMENTS 4,751,761  6/1988  Breitschmid ............... 15/176
4,780,923  11/1988  Schultheiss ................ 15/111
5,029,358  7/1991  Zimmerman ............ 15/167.1

FOREIGN PATENT DOCUMENTS 9014271.3  10/1990  Germany.

*Primary Examiner*—Edward L. Roberts, Jr.
*Attorney, Agent, or Firm*—Fish & Richardson

[57]               ABSTRACT

The invention is directed to a brush holder for a toothbrush, in particular for cleaning the interproximal spaces, for releasably locating a brush preferably comprising an in particular stem-shaped bristle supporting structure having bristles secured thereto, with the bristle supporting structure including a portion carrying no bristles, and the brush holder including a receiving structure adapted to receive the bare portion. The brush holder is of an approximately disk-shaped configuration. The receiving structure is associated with a recess, and the recess carries pivotally therein a clamping structure for clampingly, yet releasably, positioning the brush in its proper location relative to the brush holder.

13 Claims, 2 Drawing Sheets

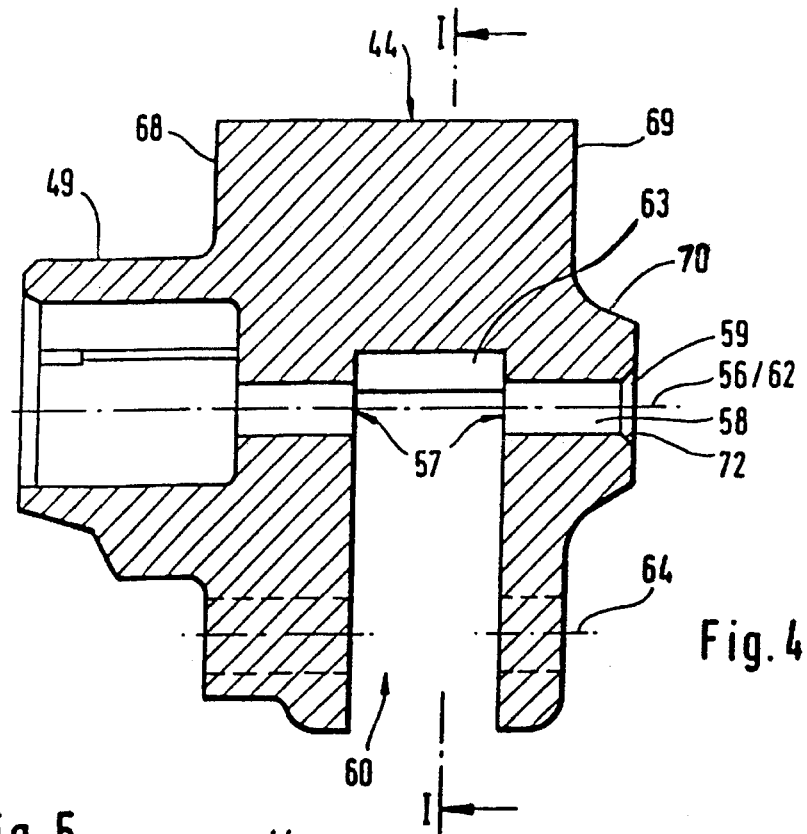
Fig. 4
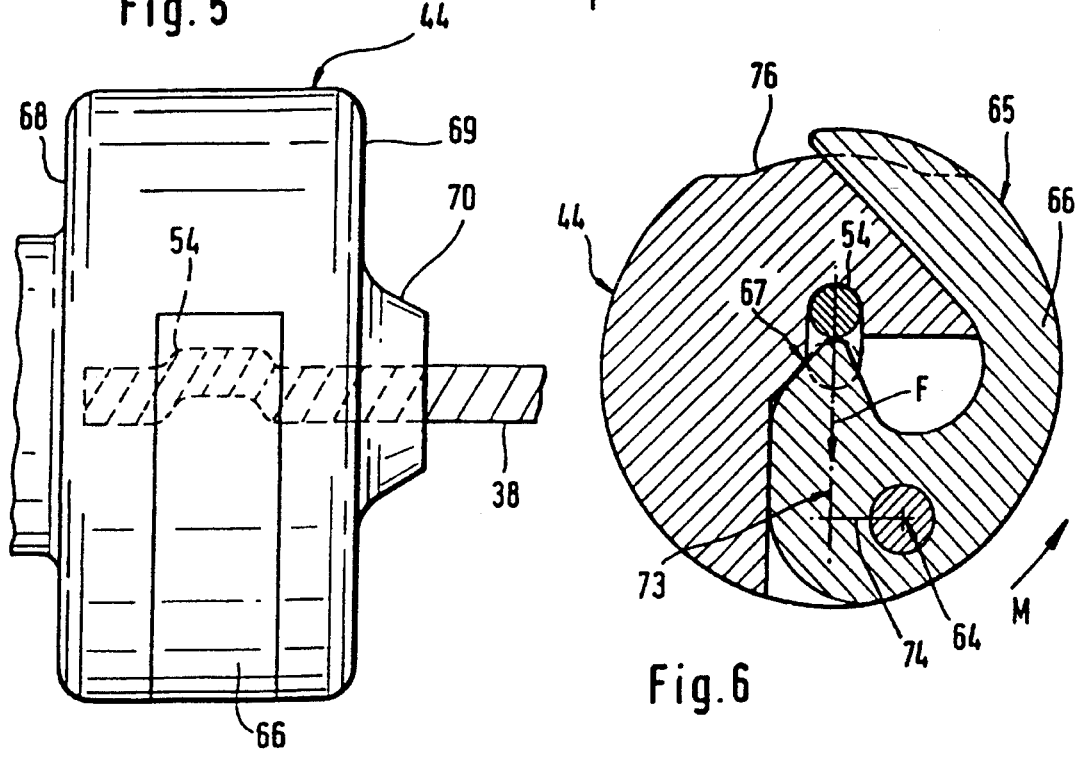
Fig. 5
Fig. 6

BRUSH HOLDER FOR A TOOTHBRUSH

This invention relates to a brush holder for a toothbrush, in particular for cleaning the interproximal spaces, for releasably locating a brush preferably comprising an in particular stem-shaped bristle supporting structure having bristles secured thereto, with the bristle supporting structure including a portion carrying no bristles, and the brush holder including a receiving means adapted to receive this bare portion.

From U.S. Pat. No. 4,780 923 A, a brush holder for interproximal brushes is known which is configured as a handle. Provided at the upper end of the handle is a transverse hole for receiving the stem of the interproximal brush. Using a cap pivotally mounted on the handle, the stem is bent at an angle of about 90°, to be received in a longitudinal groove in the handle. The cap covers the stem, including in one embodiment a latching means adapted to engage into a recess on the handle. The stem of the bristle supporting structure is thereby clampingly secured in position. By bending the stem at right angles, the angled area is exposed to bending loads particularly in the use of brushes which are driven in a rotating/oscillating fashion. Adopting this brush arrangement to an electrically rotating or oscillating toothbrush is not readily possible.

An electrically rotating toothbrush including a disposable brush is known from DE 90 142 71 U1. This toothbrush is intended for the cleaning of fixed dental braces and in particular interproximal areas. The toothbrush is comprised of a brush handle section with an electric motor to which a drive shaft is connected which extends in a guide to the end of the brush handle section. A transmission device transmits the motion to a shaft end portion which terminates in a mounting portion for receiving the brush. The mounting portion is intended to enable the brush to be plugged-in, clamped or threaded thereto. The structure and the mode of operation of the connections referred to do not appear from the description.

The main problem underlying the present invention is to devise a brush holder by means of which an interproximal brush can be located securely, yet exchangeably. According to a secondary aspect of the present invention, it is desirable that the brush holder be suitable for utilization particularly on an electrically rotating or oscillating toothbrush.

This object is essentially accomplished with a brush holder incorporating the features initially referred to, in that the brush holder is of an approximately disk-shaped configuration, that the receiving means is associated with a recess, and that the recess carries pivotally therein a clamping means for clampingly, yet releasably, positioning the brush in its proper location relative to the brush holder. The disk-shaped configuration of the brush holder is beneficial particularly because its substantially closed form prevents the possibility of injury in the mouth and gum areas in the use of the toothbrush. The use of a clamping means enables the brush to be detachably secured to the brush holder without adversely affecting the mode of function of the brush.

Advantageously, the clamping means has a pivot axis extending parallel to a center line of the receiving means. This enables the force of the clamping means to act on the stem-shaped bristle supporting structure at right angles, resulting in high efficiency and a secure clamping of the brush in its proper location with relatively little effort. Moreover, in contrast to brushes in which the stem of the bristle supporting structure is bent at right angles for the purpose of securing it to the brush holder, the risk of fracture can be significantly reduced or avoided entirely.

By providing for the recess to terminate in a section of the receiving means, and for the receiving means to include an enlarged portion adjacent to this section, the stem-shaped bristle supporting structure is in a position to enter the enlarged portion when acted upon by the clamping means, being exposed to a minor deformation in the process. Owing to this deformation, the brush is securely captured so as to prevent it from being accidentally pulled out during use.

Advantageously, by configuring the receiving means as a bore, it is possible to receive and guide the stem-shaped bristle supporting structure accurately.

By providing the bore with a diameter slightly larger than that of the stem-shaped bristle supporting structure, an additional clamping action of the bristle supporting structure within the bore can be accomplished merely by using a small untwisting motion of the wire-wound stem in use.

Advantageously, the brush holder includes an upper end having a frusto-conical projecting portion with the bore being arranged in the center thereof. The projecting portion serves to secure the stem-shaped bristle supporting structure truly axially in addition to extending the length of the guide.

In a further feature, the bore includes an entrance opening having a countersunk portion, thereby making it easier for the user to attach the replacement brush, thus facilitating manipulation.

Because the pivot axis of the clamping means is disposed in a laterally offset relation to a longitudinal center plane of the brush holder, the wire restoring force produces, through a lever arm formed between a line of force application and the pivot axis, a torque acting in the closing direction of the clamping means. This arrangement ensures that the clamping means does not inadvertently open during operation of the toothbrush.

Advantageously, the clamping means is substantially configured as a hook-shaped clamping lever having at one end of the hook a nose-shaped section which, in acting on the section of the bristle supporting structure, urges it out of its position, deforming it a small amount. This deformation occurs in the shape of a crank without major angles or bends.

In a further feature of the present invention, the brush holder is adapted to be driven in a rotating or oscillating fashion and includes an axis of rotation substantially coinciding with the center line of the receiving means. This allows the utilization of interproximal brushes also on electrically powered toothbrushes, with the coincident relationship of axis of rotation and center line of the receiving means resulting in a concentric arrangement of the receiving means in the brush holder, thus locating the brush centrally.

In an advantageous embodiment, the brush holder is configured so as to be essentially symmetrical about the axis, which ensures smooth and quiet running of the brush when driven to rotate or oscillate. In addition, this configuration prevents the possibility of injury in the use of the toothbrush.

In a further feature, the recess and the clamping means have essentially conforming length and width dimensions, as a result of which the clamping means can be nearly completely embedded within the recess. This avoids any risk of injury by parts that may protrude from the brush holder.

According to a feature of the present invention, a recess is provided between a hook end of the clamping lever and the brush holder. This recess allows manual intervention for actuating the clamping means, in addition to facilitating manipulation of the toothbrush when the brush is in need of replacement.

Further features, advantages and application possibilities of the present invention will become apparent from the subsequent description of an embodiment illustrated in more detail in the accompanying drawings. It will be understood that any single feature and any combination of single features described and/or represented by illustration form the subject-matter of the present invention, irrespective of their summarization in the claims and their back-references. In the drawings, FIG. 1 is a schematic side view of an electric toothbrush;

FIG. 4 is a longitudinal sectional view of a brush holder shown without clamping means;

FIG. 5 is a side view of a brush holder showing a stem-shaped bristle supporting structure; and FIG. 6 is a sectional view of a brush holder taken along the line I—I of FIG. 4, shown with clamping means.

Figure 1:
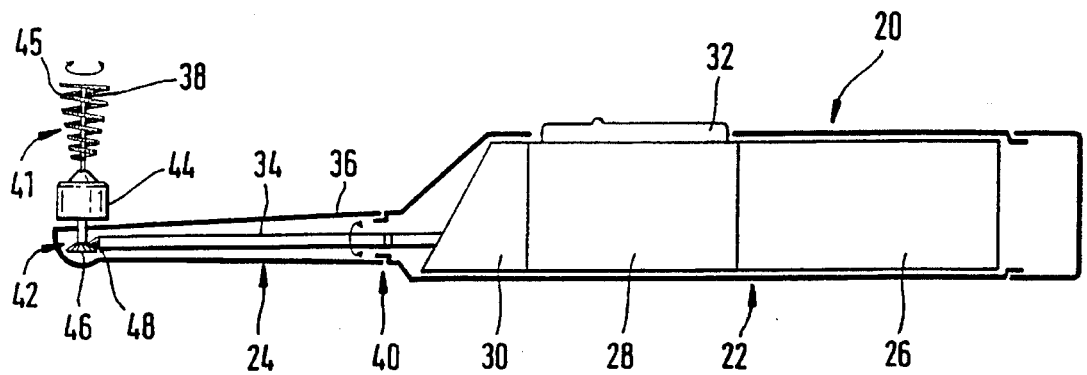
Figure 2:
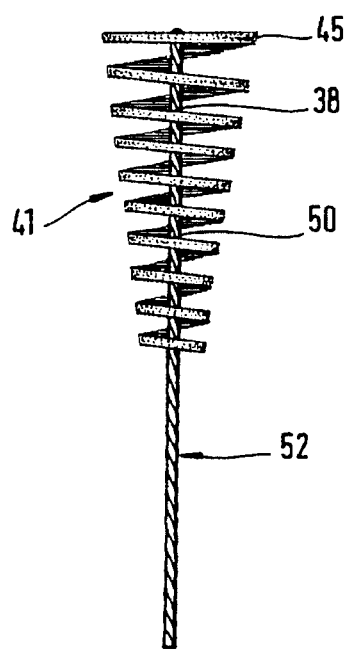
FIG. 2 is a view of an interproximal brush showing it prior to being located on the brush holder.
Figure 3:
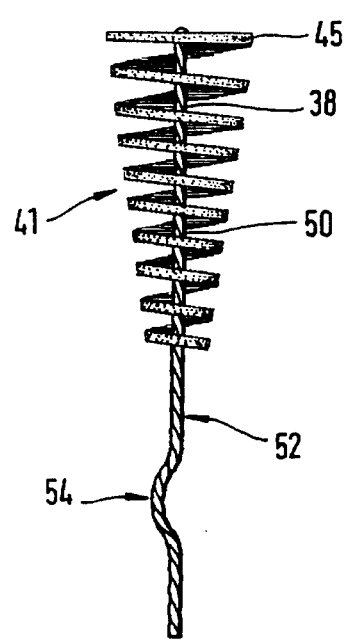
FIG. 3 is a view of an interproximal brush showing it after it has been located on the brush holder.

Referring now to FIG. 1, reference numeral 20 identifies an electric toothbrush. The toothbrush 20 is comprised of a handle member 22 and a brush member 24 adapted to be coupled thereto. The handle member 22 accommodates an accumulator 26 or, alternatively, a battery. The handle member 22 further receives in its interior an electric motor 28 and a converter arrangement 30 for converting the continuous rotary motion of the electric motor into a rotary motion reversing direction in alternating sequence. A switch 32 for activation of the toothbrush 20 is provided on the outside of the handle member 22. The brush member 24 includes a hollow mounting tube 36 receiving a shaft 34. The mounting tube 36 and the shaft 34 are adapted to be connected with the handle member 22 by a coupling means 40 not shown in greater detail. Arranged at the end of the brush member 24 remote from the handle member 22 is a brush 41 which is fixedly secured to a brush holder 44. The brush 41 includes a rod-shaped stem 38 serving as a bristle supporting structure from which circumferentially distributed bristles 45 extend in a radial direction. It will be understood, of course, that this circumferential distribution need not be in a uniform pattern. The bristles may, of course, also be locally concentrated so that the bristles are more or less thickly set in alternating sequence. Through a bevel gear arrangement 42, the shaft 34 imparts to the brush holder 44 a rotary motion reversing direction in alternating sequence. To accomplish this, a bevel gear 46 arranged at the foot of the brush holder 44 cooperates with a bevel gear segment 48 provided at the head end of the shaft 34.

The axis of rotation of the brush holder 44 or of the brush 41 defines a substantially right angle with respect to the axis of rotation of the shaft 34 or a common longitudinal axis of the handle member 22 and the brush member 24. However, this angle may also depart from the right angle by an amount of ±60° without limiting the present invention. The range of the angle of rotation covered by the brush holder 44 or the brush 41 may assume values in the range of between ±20° and ±100°. A value in the range of about ±35° ±5° is, however, preferred. The toothbrush of FIG. 1 is described in detail in applicant's International Patent Application Publication No. WO 91/07116 (corresponding to U.S. patent application Ser. No. 07/855,640), the disclosure content of which is incorporated in the present application by express reference.

An interproximal brush in undeformed condition, that is, prior to being located on the brush holder, includes a stem-shaped bristle supporting structure 38 extending rectilinearly and comprised of a bristled portion 50 and a portion 52 carrying no bristles, with the brush 41 being set with bristles 45 of, where applicable, different density essentially in the upper half of the stem-shaped bristle supporting structure 38.

When detached from the brush holder 44, the stem-shaped bristle supporting structure 38 has in one section 54 thereof a minor deformation in the form of a crank, but without any sharp bends or edges.

The brush holder 44 includes a receiving means 57 configured as a bore 58, its center line 62 coinciding with the axis of rotation 56 of the brush holder 44. A recess 60 terminates with a section thereof in the receiving means 57 which includes an enlarged portion 63 adjacent to this section. A pivot axis 64 in parallel arrangement with the axis of rotation 56 serves to receive the clamping lever 66. The upper end 69 of the brush holder 44 has a frusto-conical projecting portion 70 receiving in its center the bore 58 which includes an entrance opening 59 on which a countersunk portion 72 is formed. Provided at the lower end 68 of the brush holder 44 is a sleeve section 49 serving to receive a pin which transmits the rotary or oscillatory motion to the brush holder 44. This connection and the driving mechanism are described in detail in International Patent Application No. WO 91/07116 referred to.

A side view of a brush holder 44 is shown in FIG. 5. In clamped condition, the clamping lever 66 is received within the recess 60, and its effect on the stem-shaped bristle supporting structure 38 becomes apparent when viewing the deformed section 54. In addition to preventing the brush 41 from being pulled out, this positive-engagement relationship of the clamping lever 66 to the stem-shaped bristle supporting structure 38 ensures that the brush 41 is compelled to follow the brush holder 44 in rotation or oscillation. The projecting portion 70 provides an additional guide for the stem-shaped bristle supporting structure 38.

In the closed position of the clamping means 65 configured as clamping lever 66, the nose-shaped section 67 has displaced the stem-shaped bristle supporting structure 38 from its normal position, deforming it in section 54. The pivot axis 64 of the clamping lever 66 is arranged at a relative distance to a longitudinal center plane of the brush holder 44. The wire restoring force F produces, through the lever arm 74 formed between the line of force application 73 and the pivot axis 64, a torque M acting in the closing direction of the clamping lever 66. This prevents the undesired effect of the clamping lever 66 opening during use of the toothbrush 20. For ease of manipulation of the clamping lever 66, a recess 76 is provided between a hook end of the clamping lever 66 and the brush holder 44, enabling the clamping lever to be readily accessible when in the closed position, while yet being practically fully embedded within the recess.

I claim:

1. A brush holder for a toothbrush for cleaning the interproximal spaces, said brush holder for releasably locating a brush including a stem-shaped bristle supporting structure having bristles secured thereto, the bristle supporting structure including a bare portion carrying no bristles, said brush holder comprising an approximately disk-shaped body having a receiving means adapted to receive the bare portion of the stem-shaped structure, said body also having a recess proximate to said receiving means, and said brush holder also comprising a clamping means that the recess carries pivotally therein, said clamping means for clampingly, yet releasably, positioning the brush in its proper location relative to the brush holder.

2. A brush holder as claimed in claim 1, wherein the clamping means pivots about a pivot axis extending parallel to a center line of the receiving means.

3. A brush holder as claimed in claim 2, wherein the recess extends into the receiving means and wherein the receiving means includes an enlarged portion adjacent to where the recess extends into the receiving means.

4. A brush holder as claimed in claim 3 wherein the receiving means is configured as a bore.

5. A brush holder as claimed claim 4 wherein the bore is provided with a diameter slightly larger than that of the stem-shaped structure.

6. A brush holder as claimed in claim 4, wherein said body includes an upper end having a frusto-conical projecting portion with the bore being arranged in the center thereof.

7. A brush holder as claimed in claim 6, wherein the bore (58) includes an entrance opening having a countersunk portion.

8. A brush holder as claimed in claim 2, wherein the clamping means is substantially configured as a hook-shaped clamping lever having at one end a nose-shaped section.

9. A brush holder as claimed in claim 2 wherein the brush holder is adapted to be driven in a rotating or oscillating fashion about an axis of rotation substantially coinciding with a center line of the receiving means.

10. A brush holder as claimed in claim 9, wherein the brush holder is configured so as to be essentially symmetrical about the axis of rotation.

11. A brush holder as claimed in claim 1 wherein the pivot axis of the clamping means is laterally offset from a longitudinal center plane of the brush holder.

12. A brush holder as claimed in claim 1 wherein the recess and the clamping means are substantially the same size.

13. A brush holder as claimed in claim 12, further comprising a second recess between a hook end of the clamping lever and the body of the brush holder.

\* \* \* \* \*